(12) United States Patent
Horber

(10) Patent No.: US 6,537,321 B1
(45) Date of Patent: *Mar. 25, 2003

(54) JOINT BASE FOR A HIP JOINT ENDOPROSTHESIS

(75) Inventor: Willi Horber, Zürich (CH)

(73) Assignee: Plus Endoprothetik AG, Rotkreuz (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,762
(22) PCT Filed: Nov. 21, 1997
(86) PCT No.: PCT/EP97/06515
  § 371 (c)(1),
  (2), (4) Date: Jul. 19, 1999
(87) PCT Pub. No.: WO98/22049
  PCT Pub. Date: May 28, 1998

(30) Foreign Application Priority Data

Nov. 21, 1996 (DE) .......................... 196 48 263
Jan. 20, 1997 (DE) .......................... 197 01 778

(51) Int. Cl.[7] ................................................ A61F 2/32
(52) U.S. Cl. ........................ 623/22.22; 623/22.24; 623/22.32
(58) Field of Search .................... 623/22.19, 22.21, 623/22.32, 22.34, 22.35, 22.36, 22.38, 22.22, 22.24, 23.13, 23.43, 19.11–19.13, 20.33, 22.31

(56) References Cited

U.S. PATENT DOCUMENTS

| | | | | |
|---|---|---|---|---|
| 3,840,904 A | * | 10/1974 | Tronzo | .................... 623/22.32 |
| 3,903,549 A | * | 9/1975 | Deyerle | .................... 623/22.28 |
| 4,822,362 A | | 4/1989 | Walker et al. | |
| 4,938,769 A | | 7/1990 | Shaw | |
| 5,192,329 A | | 3/1993 | Christie et al. | |
| 5,201,768 A | | 4/1993 | Caspari et al. | |
| 5,314,490 A | * | 5/1994 | Wagner et al. | ................. 623/22 |
| 5,356,414 A | | 10/1994 | Cohen et al. | |
| 5,370,703 A | * | 12/1994 | Willert et al. | ............ 623/22.22 |
| 5,413,605 A | | 5/1995 | Ashby et al. | |
| 5,480,448 A | * | 1/1996 | Mikhail | .................... 623/22.24 |

FOREIGN PATENT DOCUMENTS

| | | |
|---|---|---|
| DE | 7240856 | 2/1973 |
| DE | 2 301 810 | 7/1973 |
| DE | 26 11 985 | 9/1977 |
| DE | 28 02 655 | 8/1978 |
| DE | 30 13 155 | 10/1980 |
| DE | 42 30 118 | 8/1995 |
| EP | 0 384 854 | 10/1992 |
| EP | 0 551 791 | 7/1993 |
| EP | 0 552 949 | 7/1993 |
| EP | 0 585 503 | 3/1994 |
| EP | 0 611 559 | 8/1994 |
| EP | 0 636 353 | 2/1995 |
| EP | 0 709 074 | 5/1996 |
| EP | 0 709 075 | 5/1996 |
| FR | 2 700 263 | 7/1994 |
| WO | 15261 | * 9/1992 |
| WO | WO 95/24874 | 9/1995 |

\* cited by examiner

Primary Examiner—Bruce Snow
Assistant Examiner—Brian E Pellegrino
(74) Attorney, Agent, or Firm—Knobbe, Martens, Olson & Bear, LLP

(57) ABSTRACT

A joint base for a hip joint endoprosthesis includes an elongate base element and a base insert. The base element has a longitudinal axis and an outline which, in a front view, is of asymmetrical design at least relative to the longitudinal axis. The base insert has at a front side a semi-spherical hollow for accommodating a joint ball.

19 Claims, 5 Drawing Sheets

JOINT BASE FOR A HIP JOINT ENDOPROSTHESIS

FIELD OF THE INVENTION

The invention relates to a joint base for a hip joint endoprosthesis, comprising a base element of elongated shape and a base insert (inlay) which has at the front side a semi-spherical hollow for accommodating a joint ball.

BACKGROUND OF THE INVENTION

Endoprostheses as hip joint replacement have been known for a long time. Reference is made to DE-U 72 40 856 or DE-A 26 11 985. In the DE-A 23 01 810 is described a joint base consisting of an outer and an inner cup, and the inner cup is detachably accommodated in the outer cup and itself accommodates a joint ball. In the EP-B 0 303 006 is described a revision base, which is thus suited in particular as replacement for an implanted joint base with detailed base roof of the acetabulum. This joint base includes a base element which has at the front side a semi-spherical hollow for accommodating a joint base, and the axis of the hollow lies eccentrically of the base element and the joint base is cross-sectionally perpendicular to the eccentrically lying axis of the hollow of elongated oval shape. Thus, the known joint base provides a joint element of elongated shape which is symmetrical both in the longitudinal direction and in the transverse direction thereto, i.e. virtually forming an oval. The semi-spherical hollow preferably lies in an area in which the anatomic hollow is positioned in the acetabulum. The idea of this design is that the joint base closely resembles the anatomy as it develops by a loosened prosthetic joint base with the base roof wearing down. Accordingly, insertion of the joint base requires only minimal removal or replacement of bone substance for insertion of the joint base.

However, a disadvantage of the prior art is the symmetrical design of the joint base, as a result of which usually only so-called two-point tensioning of it inside the acetabulum can be achieved. Around the connecting line between these two points, tilting moments become effective which after an extended period of implantation can result in loosening of the base. Then, the joint base has to be again replaced.

SUMMARY OF THE INVENTION

It is an object of the present invention to produce a joint base of the aforementioned type which permits statically determined tensioning within the acetabulum, so that no tilting moments can become active which result in loosening of the base. It is a particular aim to achieve defined multi-point tensioning.

An object of the invention involves a joint base for a hip joint endoprosthesis. The joint base includes an elongate base element and a base insert. The joint base has a longitudinal axis and an outline which, in a front view, is of asymmetrical design at least relative to the longitudinal axis. The base insert has at a front side a semi-spherical hollow for accommodating a joint ball. In this respect, reference is made to an embodiment, according to which the joint base has, as seen in a frontal view, amongst other things a kidney- or beanshaped outline. This outline results in three-point tensioning at the convex extreme points. This tensioning is statically determined and as such accordingly stable.

Alternatively, the outline of the joint base could be of trapezoidal, triangular, halfmoon, heart, arrow or semi-circular or similar asymmetrical shape. It only has to be ensured that statically determined multi-point tensioning is achieved in order to obtain a stable implantation.

Furthermore, an aspect of the invention involves an embodiment, according to which the base insert is fixed within a corresponding cutout in the joint base, i.e. in different angular positions relative to the center axis of the aforementioned cutout, and the cutout is preferably of concentrical design in the base element. For an eccentrically arranged semi-spherical hollow in the base insert, this hollow can then be placed into a desired position relative to the base element. Thus, both the cranio/caudal (i.e., top/bottom) position of the semi-spherical hollow as well as its medio/lateral position can be varied. This is of advantage when the base cannot be implanted in an ideal position due to bone defects.

Furthermore, an aspect of the invention involves an embodiment, according to which the front of the base element is in the cranial area covered in a forward direction whilst it is retracted toward the inside or rear in the caudal area. By covering in the cranial area, a luxation of the joint ball in the steep position of the base is prevented. In this case, retraction in the caudal area also permits sufficient adduction of the leg.

It is also of advantage if the bottom of the base element comprises one or more passages which is/are closable by a sealing cover, in particular a displaceably or rotary mounted sealing cover. This makes it possible, after insertion of the base element into the pelvis of the patient, to control the setting depth and spongiosa between bone and bottom of the base element. In order to prevent contact between the base insert or inlay, which is preferably made of plastic, and the bone, the aforementioned passage in the bottom of the base element is sealed with a sealing cover, i.e. preferably a rotary mounted sealing cover. An alternative solution provides shaping the rear or outside of the base insert of the same material or a similar material as the base element and in such a manner that on insertion of the base insert into the base element the rear of the base insert closes one or more passages in the bottom of the base element like a sealing cover. This solution is very advantageous in particular for handling or manufacturing.

In order to additionally increase fixing of the base element, the latter may comprise at the outside a plurality of engagement webs with knifelike cutters spaced virtually evenly over the circumference, and the engagement webs extend approximately parallel to the center axis of the joint element.

Furthermore, the base element can for this purpose comprise holes in the cranial and/or caudal area for passing through bone screws, and the screw holes are preferably like a sand-glass or venturi-tube so that the screws can be screwed in without force at different angles. It is also possible to provide bungs for closing unused screw holes. The screw holes are preferably located between the aforementioned engagement webs of the base element.

Fixing the base insert in a corresponding cutout of the base element is advantageously achieved by a snap-on mechanism. It is feasible to provide for this purpose at the outside of the base insert a peripheral bead which engages a corresponding annular groove within the cutout of the base element.

The surface of the semi-spherical hollow configured in the base insert is preferably provided with a gliding layer, in particular a gliding layer of metal, ceramic or a friction resistant plastic material. The base insert can also be made in total of one of the aforementioned materials, in particular ceramics or a combination of these materials.

For the purpose of fixing the base insert within a corresponding cutout in the base element at a predetermined angle relative to the center axis of the aforementioned cutout, the base insert can have at the side of the edge at least one radially outward extending protrusion or alternatively at least one recess, which correspond(s) with at least one recess in the cutout of the base element or one protrusion in the cutout of the base element. Preferably a plurality of protrusions or recesses is arranged evenly spaced over the circumference.

BRIEF DESCRIPTION OF THE DRAWINGS

Below, a preferred form of embodiment of a joint base designed according to the invention will be explained in more detail, based on the attached drawings. Shown are, in FIG. 1 a base element according to the invention, in a side view.

DETAILED DESCRIPTION OF THE INVENTION

FIGS. 1 to 4 show an elongated base element 10 of a joint base for a hip joint endoprosthesis. FIGS. 5 to 8 show a rotary-symmetrical base inlay 11 having at the front side a semi-spherical hollow 12 to accommodate a joint ball (not illustrated). Base inlay 11 is intended for accommodation within a corresponding cutout 13 in base element 10.

Figure 1:
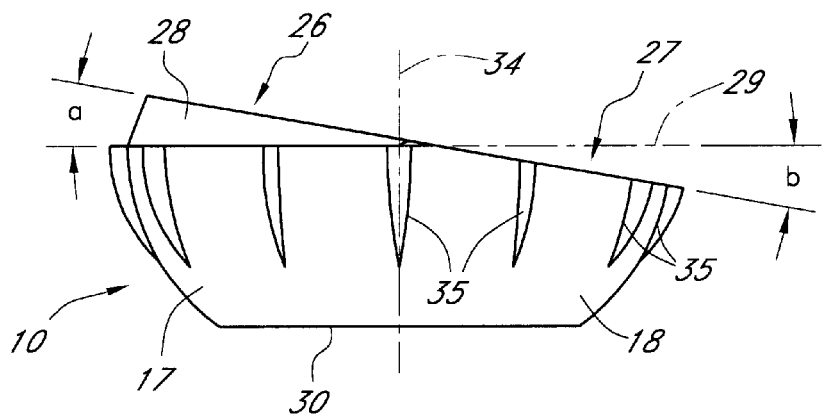
Figure 2:
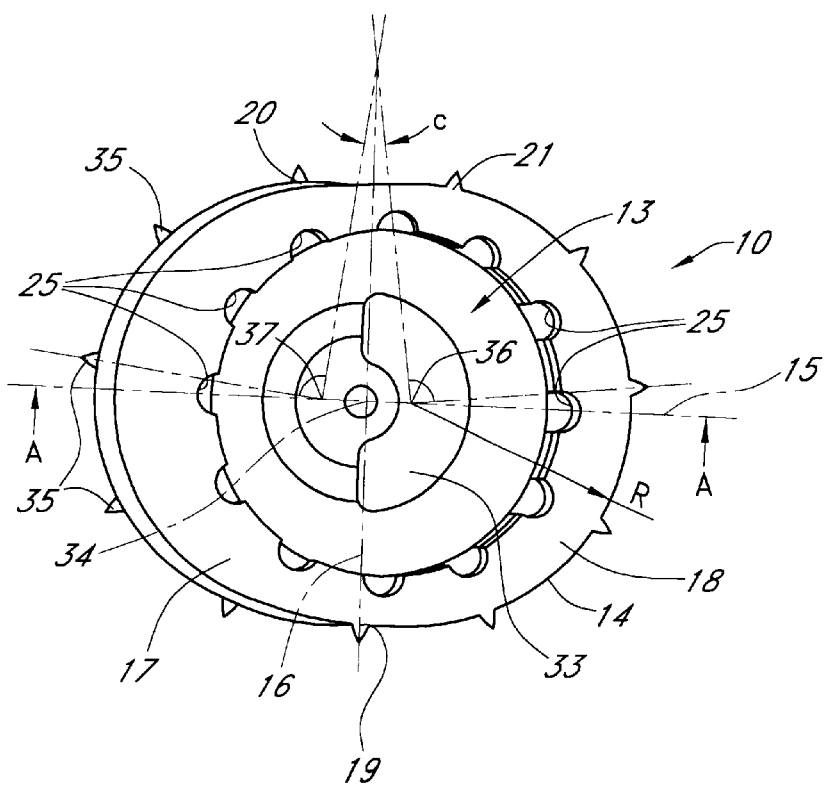
FIG. 2 a base element according to the invention, in a top view.

FIG. 2 shows very well that base element 10 is of elongated shape, as seen in a front and top view, and outline 14 is an asymmetrical design relative to longitudinal axis 15. In the illustrated form of embodiment, the outline of base element 10 is, in a front or top view, concretely designed in the shape of a kidney or bean. This outline is established by connecting or bridging two quarter-spherical cups 17 and 18, which lie opposite each other at angle "c" relative to transverse axis 16 of base element 10, and these quarter-spherical cups are at the bottom flattened as in FIGS. 1 and 3. At this point, it may be mentioned that the base element can also be defined by the described joining of halves or sections of two rotary elements, such as ball segments, ball hoods, cones, cylinders or the like or also by prismatic elements rather than by quarter-spherical cups. With such shape elements, the rotary or symmetry axes, which lie essentially parallel to center axis 34 which is mentioned further down, then replace the ball center points.

Furthermore, ball centers associated with the quarter spherical cups are at a distance from each other. Base element 10 is then symmetrical relative to transverse axis 16, but not relative to longitudinal axis 15. This achieves so-called three-point tensioning within the acetabulum, i.e. at the convex extreme points which are denoted 19, 20 and 21 in FIG. 2. This ensures a lasting stable implantation, in particular free of cement, of base element 10 within a correspondingly detailed acetabulum.

The base element is made of a body-compatible metal, for example a cobalt chrome molybdenum alloy, titanium or titanium alloy.

Base inlay 11 illustrated in FIGS. 5 to 8 is preferably made of a body compatible material such as metal, ceramic or plastic, in particular polyethylene or the like, on its own or in a combination thereof.

Base inlay 11 is fixed within the aforementioned recess 13 in base element 10, i.e. in the illustrated form of embodiment in different angular positions relative to center axis 22 of cutout 13, and this recess 13 is preferably of concentric design in base element 10. Deviating therefrom, cutout 13 in the illustrated form of embodiment is caudially transposed. Furthermore, the entry plane of cutout 13 is slanted from cranial to caudal by angle "d".

Base inlay 11 is of rotary-symmetrical design, i.e. semi-spherical. It is fixable in a positive and flush manner within corresponding cutouts 13 in base element 10. For this purpose, base insert 11 has at the edge four protrusions 24, which are evenly spaced over the circumference and which extend radially outward and which correspond with a plurality of recesses 25 which are arranged evenly over the circumference and diametrically to each other in cutout 13 of base element 10 in such a manner that the angular position of base inlay 11 is freely selectable. Furthermore, semi-spherical hollow 12 of base inlay 11 is arranged eccentrically, i.e. in such a manner that after insertion of the base inlay into the base element the ball center of semi-spherical hollow 12 is, depending on the angular position of the base insert, exactly at the height of transverse axis 16 of base element 10 (angular position 0 degrees) or caudally thereto, and the maximum caudal distance at an angular position of 180 degrees is achieved. By varying the angular position, it is possible to vary not only the cranio/caudal position of the ball center but also the medio/lateral position relative to longitudinal axis 15 of base element 10. This offers an advantage if the base cannot be implanted in an ideal position due to bone defects.

Figure 3:
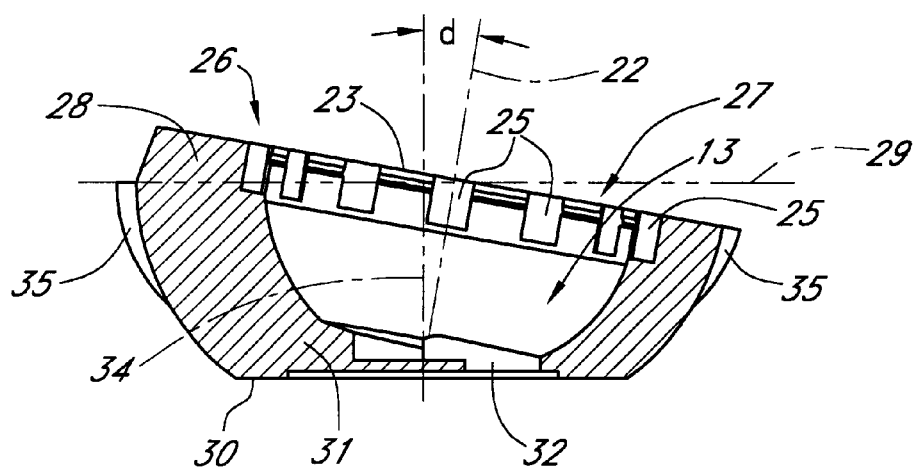
FIG. 3 the base element as in FIG. 2, cross-sectionally along line A—A in FIG. 2.

According to FIGS. 1 and 3, the front of base element 10 is in cranial area 26 covered towards the front (front cover 28). In caudal area 27, the front of base element 10 is retracted towards the inside or the rear. Front cover 28 is at an angle "a", whilst caudal retraction is at an angle "b". These angles are given with reference to a main base plane 29 which extends parallel to flattening 30 of the bottom of the base element 10. Angles "a" and "b" can be equal or different size. It is also feasible to provide only one front cover and no retraction, or only a retraction and no front cover.

Flush fixing of base inlay 11 within cutout 13 of base element 10 by means of protrusions or naps 24 arranged at the peripheral edge of base inlay 11 and corresponding recesses 25 arranged at the front peripheral edge of recess 13 can be replaced by purely positive fixing without protrusions and recesses. This purely positive fixing permits random angular position of base inlay 11 within cutout 13 in base element 10.

Bottom 31 of base element 10 comprises a passage 32 which can be sealed by a sealing cover 33. Sealing cover 33 is rotary mounted around axis 34 which extends perpendicularly to bottom 31. Bottom opening 32 then extends only over a predetermined circular sector which is sealed by a matching sectorial sealing cover. Sealing cover 33 is designed as a sectorial lamellar disc.

Passage 32 makes it possible to control, after insertion of base element 10 into acetabulum, the setting depth and/or to enter spongiosa between the bottom of base element 10 and the bone. Thereafter, passage 32 is sealed by means of sealing cover 33, so that base insert 11 does not make contact with the bone.

Figure 4:
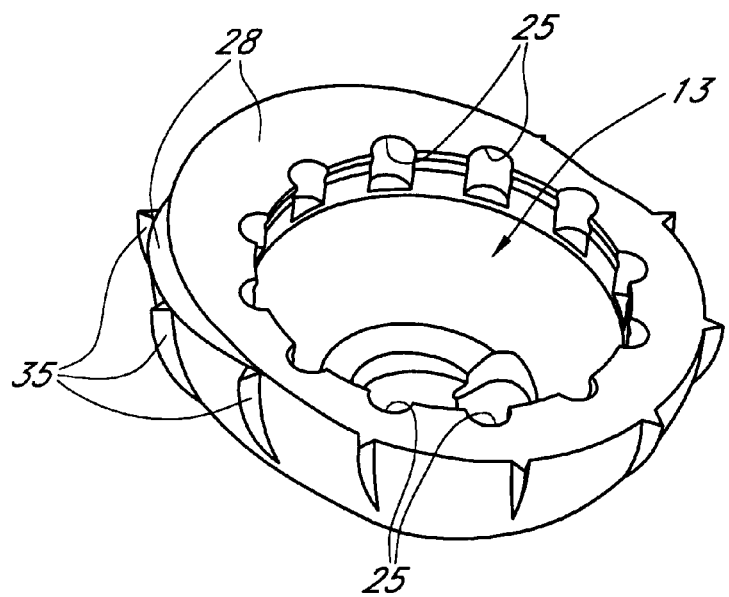
FIG. 4 the base element as in FIGS. 1 to 3, in a perspective view transversely from above.
Figure 5:
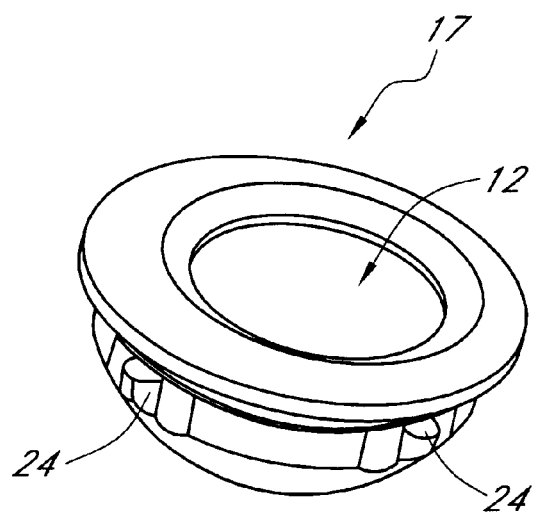
FIG. 5 a base insert (inlay) for the base element as in FIGS. 1 to 4, in a perspective view transversely from above.
Figure 6:
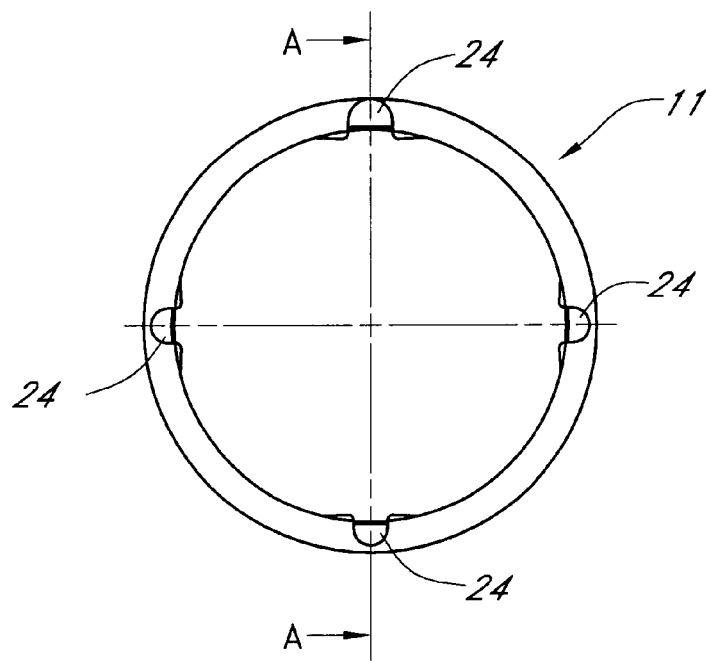
FIG. 6 bottom view of the base insert as in FIG. 5.
Figure 7:
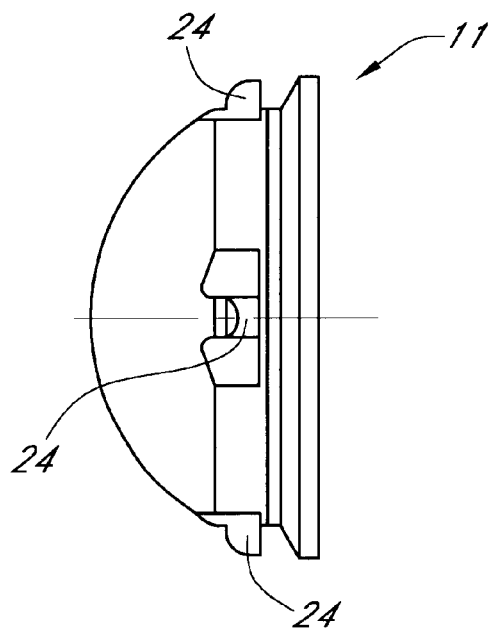
FIG. 7 the base insert as in FIG. 6, in a side view.

According to FIGS. 1, 2 and 4, base element 10 comprises externally engagement webs 35 which extend to center axis 34, i.e. a plurality of them approximately evenly spaced over the circumference of base element 10. The engagement webs are radially and externally provided with knifelike cutters. These engagement webs permit even more stable anchorage of the base element in the pelvis bone. If required, they can reach as far as to front cover 28.

Base element 10 can have holes in the cranial and/or caudal area for passing through bone screws, and the screw holes are preferably of sand glass or venturi tube type so that the screws can be screwed in at different angles without force. If required, the screw holes can be sealed by bungs, screws or the like. The screw holes preferably extend between two adjacent engagement webs 35.

Fixing of base inlay 11 in corresponding cutout 13 of base element 10 is preferably carried out by a snap-on mechanism, in particular a protrusion which engages an annular groove in base element cutout 13, in particular an annular bead or bead section at the outside of base insert 11. Alternatively, the annular protrusion can be formed at the inside of cutout 13 which then corresponds with an annular groove on the outside circumference of base insert 11. It is also feasible in principle to hold base insert 11 within cutout 13 of base element 10 by a separate spring washer which can be placed within an annular groove near the upper entry edge of cutout 13 and which covers the upper edge of base insert 11.

The surface of hollow 12 established in base insert 11 is preferably provided with a glide layer, in particular a glide layer of metal, ceramic or a wear-resistant plastic material.

As regards the aforementioned angles, it may be mentioned that angle "c" must be at least 10 degrees. Angles "a" and "b" are between 0 and 30, angle "a" preferably between approximately 12 and 17 degrees, and angle "b" approximately between 8 and 15 degrees.

Angle "d" corresponds approximately with the mean average of angles "a" and "b".

The centers of the aforementioned quarter-ball cups 17, 18 are characterised in FIG. 2 by reference numbers 36, 37. The distance of these two centers corresponds with the expanse of the base element in the direction of its longitudinal axis 15. The radius of quarter-ball cups 17, 18 is shown in FIG. 2 as "R". Angle "c" is a measure of curvature of the elongated base element whilst establishing a kidney or bean shape in deviation from an exact oval or ellipsoid form.

Figure 8:
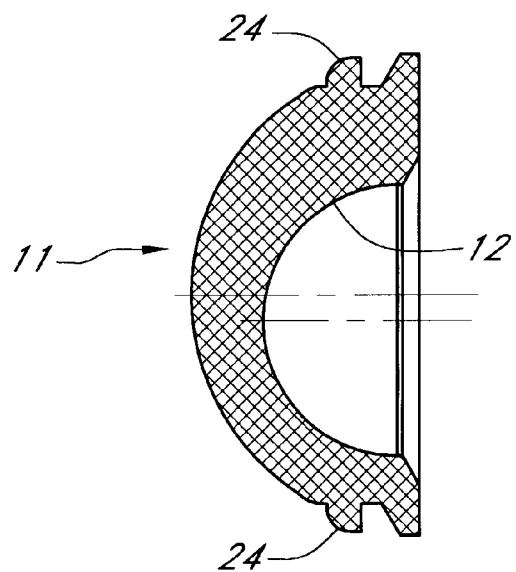
FIG. 8 the base inlay as in FIG. 6, cross-sectionally along line A—A in FIG. 6.
Figure 9:
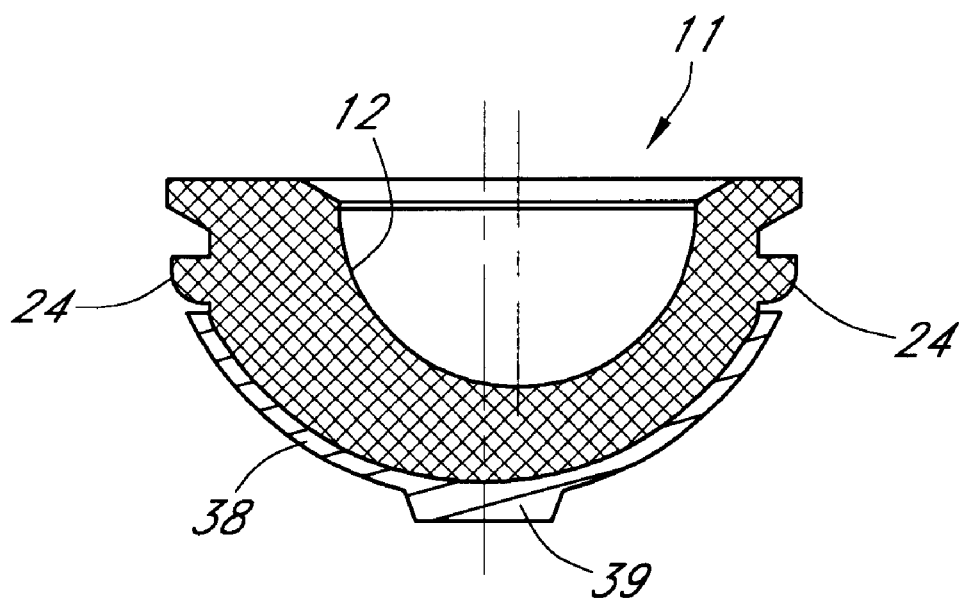
FIG. 9 a base insert with integrated cover, cross-sectionally shown.

FIG. 9 illustrates a base inlay 11 as in FIG. 8. The base inlay as in FIG. 9 differs from the one in FIG. 8 in that onto its rear or outside is formed, or in a different manner attached, a cupshaped metallic inlay sealing cover 38 with a naplike sealing element in the form of an radially outward extending protrusion 39. This inlay sealing cover 38 is a type of "metal backing". It is preferably composed of the same material as the associated base element 10. Protrusion 39, which is preferably conical, i.e. designed as a truncated cone, closes in an assembled state of base inlay and base element a corresponding passage in the base element. The base inlay is detented into the base element in such a manner that protrusion 39 guarantees a tight seal of the associated passage in the base element. Corresponding polar pretensioning on protrusion 39 is carried out by the aforementioned detention of the base inlay along the equatorial periphery in the base element. Due to this polar/equatorial clamping or detention, the titanium or similar cup 38 lying thereinbetween does not have to abut the inside surface of base element 10, in consequence of which no metal friction has to be feared. Furthermore, it is an advantage of the "metal backing" that no flow of polyethylene of base inlay 11 is to be expected in the area of the screw holes in base element 10.

All features revealed in the application documents are claimed as part of the invention as long as they are individually or in a combination new relative to the prior art.

List of Reference Marks

10—Base Element
11—Base Insert (Inlay)
12—Semi-Spherical Hollow
13—Cutout
14—Outline
15—Longitudinal Axis
16—Transverse Axis
17—Quarter-Spherical Cup
18—Quarter-Spherical Cup
19—Extreme Clamping Point
20—Extreme Clamping Point
21—Extreme Clamping Point
22—Central Axis
23—Entry Plane
24—Protrusion
25—Recess
26—Cranial Area
27—Caudal Area
28—Cover
29—Main Base Plane
30—Bottom Flattening
31—Base Element Bottom
32—Passage
33—Cover
34—Axis
35—Engagement Webs
36—Ball Center Point
37—Ball Center Point
38—Cover
39—Naplike Protrusion
c—Angle
d—Angle
a—Angle
b—Angle

What is claimed is:
1. A hip joint endoprosthesis, comprising:
an elongate base element having a longitudinal axis extending substantially in the direction of elongation and a transverse axis perpendicular to said longitudinal axis, and which, in a plan view looking into a cup portion of said base element, defines an outline formed by a circumferential outer edge of the base element, wherein the outline is of asymmetrical geometric shape at least relative to the longitudinal axis to provide for a defined multi-point tensioning within an acetabulum to ensure lasting stable implantation, and wherein the geometric shape defined by the outline of the plan view of the base element is formed by joining two circles which have centers that are spaced apart a predeter- mined distance and which are arranged relative to each other at an angle relative to a transverse axis of the base element such that one of two elongated sides of the outline formed by the circumferential outer edge of the base element has an indentation; and a base insert having a front side and, at the front side, a semi-spherical hollow for accommodating a joint ball.

2. The joint hip of claim 1, wherein the base insert comprises a body compatible material selected from the group consisting of ceramic, plastic, polyethylene, and a combination of ceramic and plastic, and wherein the base element comprises a body compatible metal selected from the group consisting of a cobalt chrome molybdenum alloy, a titanium, and a titanium alloy.

3. The joint hip of claim 1, wherein a rear side of the base insert comprises a body compatible metal selected from the group consisting of cobalt chrome molybdenum alloy, titanium and titanium alloy.

4. The joint hip of claim 3, wherein the base element comprises a bottom having at least one passage.

5. The joint hip of claim 1, wherein the semi-spherical hollow is eccentrically arranged in the base insert.

6. The joint hip of claim 1, wherein the base insert is fixed within a corresponding cutout in the base element, the cutout being configured to be concentrically in the base element.

7. The joint hip of claim 6, wherein the base insert is fixed in different angular positions relative to a center axis of the cutout.

8. The joint hip of claim 1, wherein the base insert is a rotary symmetrical cup which is fixed within a corresponding cutout in the base element, the cup having a shape selected from the group consisting of cylindrical, truncated and semi-spherically shapes.

9. The joint hip of claim 1, wherein the base element comprises an elevation mounted on a face of the base element at a cranial area of the base element.

10. The joint hip of claim 1, wherein the base element comprises a negative elevation formed in a face of the base element at a caudal area of the base element.

11. The joint hip of claim 1, wherein the base element comprises a base having a passage which is sealable by a cover mounted to be displaceable or rotable.

12. The joint hip of claim 11, wherein the cover is positioned at a rear side of the base insert.

13. The joint hip of claim 1, wherein the base element comprises engagement webs which extend externally parallel to a center axis, the engagement webs having knifelike cutters spaced approximately evenly over a circumference of the base element.

14. The joint hip of claim 1, wherein the base element comprises, in a cranial area and a caudal area, a plurality of screw holes to allow bone screws to pass through, and wherein the screw holes are shaped like a sand-glass so that the screws can be screwed in without force at different angles.

15. The joint hip of claim 14, wherein the screw holes are sealable by associated closing elements, the closing elements selected from the group consisting of bungs and screws.

16. The joint hip of claim 1, further comprising a snap-on mechanism configured to secure the base insert in a corresponding cutout of the base element, the snap-on mechanism comprising a protrusion which engages at least one of an annular groove, an annular bead and a bead section of the base insert.

17. The joint hip of claim 1, wherein a surface of the hollow established in the base insert is provided with a glide layer comprising a material selected from the group consisting of metal, ceramic and wear-resistant plastic material.

18. The joint hip of claim 1, wherein the base insert comprises at an edge at least one radially outward extending protrusion, which corresponds with at least one recess established in a cutout of the base element.

19. The joint hip of claim 1, wherein the base insert comprises at an edge at least one recess, which corresponds with at least one protrusion established in the cutout of the base element.

* * * * *

UNITED STATES PATENT AND TRADEMARK OFFICE
CERTIFICATE OF CORRECTION

PATENT NO. : 6,537,321 B1  Page 1 of 1
DATED : March 25, 2003
INVENTOR(S) : Willi Horber It is certified that error appears in the above-identified patent and that said Letters Patent is hereby corrected as shown below:

<u>Column 7, lines 8-37 through Column 8, lines 1-34,</u>
Please delete "joint hip" and insert therefore, -- hip joint --.

Signed and Sealed this

Eighth Day of June, 2004

JON W. DUDAS
*Acting Director of the United States Patent and Trademark Office*